United States Patent
Fischer et al.

(10) Patent No.: US 9,464,247 B2
(45) Date of Patent: Oct. 11, 2016

(54) DEVICE FOR THE TREATMENT OF CRUDE SYNTHESIS GAS

(71) Applicant: SIEMENS AKTIENGESELLSCHAFT, München (DE)

(72) Inventors: Norbert Fischer, Lichtenberg (DE); Manfred Jänig, Grünewald (DE); Doris Klostermann, Freiberg (DE); Andreas Meissner, Trebsen/Mulde (DE); Manfred Schingnitz, Freiberg (DE); Guido Schuld, Dresden (DE)

(73) Assignee: SIEMENS AKTIENGESELLSCHAFT (DE)

( * ) Notice: Subject to any disclaimer, the term of this patent is extended or adjusted under 35 U.S.C. 154(b) by 0 days.

(21) Appl. No.: 14/456,196

(22) Filed: Aug. 11, 2014

(65) Prior Publication Data

US 2015/0045457 A1 Feb. 12, 2015

(30) Foreign Application Priority Data

Aug. 9, 2013 (DE) .......... 10 2013 215 804
Feb. 27, 2014 (DE) .......... 10 2014 203 593

(51) Int. Cl.
*C10K 1/02* (2006.01)
*C07C 1/04* (2006.01)
(Continued)

(52) U.S. Cl.
CPC . *C10K 1/02* (2013.01); *C07C 1/04* (2013.01); *C07C 1/041* (2013.01); *C10G 2/30* (2013.01); *C10J 3/466* (2013.01); *C10J 3/54* (2013.01); *C10J 3/56* (2013.01); *C10K 1/003* (2013.01); *C10K 1/101* (2013.01); *C10K 3/04* (2013.01); *C10K 3/06* (2013.01); *C10J 2300/093* (2013.01); *C10J 2300/1656* (2013.01)

(58) Field of Classification Search
CPC combination set(s) only.
See application file for complete search history.

(56) References Cited

U.S. PATENT DOCUMENTS

| | | | |
|---|---|---|---|
| 7,744,665 B2* | 6/2010 | Holle et al. ............. | 48/210 |
| 2004/0047799 A1* | 3/2004 | Randhava ............. | B01J 8/0465 423/652 |
| 2007/0044381 A1 | 3/2007 | Holle et al. | |
| 2012/0023822 A1* | 2/2012 | D'Agostini et al. ........... | 48/61 |
| 2012/0039776 A1* | 2/2012 | Ghosh ............. | 422/608 |

FOREIGN PATENT DOCUMENTS

| | | |
|---|---|---|
| DE | 44 46 803 A1 | 6/1996 |
| DE | 10 2005 041 930 | 3/2007 |
| EP | 0 677 567 B1 | 9/1997 |

OTHER PUBLICATIONS

Schmalfeld J. et al: "Die Veredlung und Umwandlung von Kohle", Technologien und Projekte 1970 bis 2000 in Deutschland, Deutsche Wissenschaftliche Gesellschaft für Erdöl, Erdgas und Kohle e.V., Kapitel 4.4.2 Gaskombinat Schwarze Pumpe-Verfahren (GSP), pp. 537-552, Dec. 2008.

(Continued)

*Primary Examiner* — Matthew Merkling
(74) *Attorney, Agent, or Firm* — Ostrolenk Faber LLP

(57) ABSTRACT

A device for treating steam-saturated crude gases from the entrained flow gasification of fuels before entry into heat exchanges sited upstream of a crude gas converting operation. To avoid solid deposits in an entrance region of the heat exchangers, a crude gas is converted from a saturated into the superheated state by supply of hot gas. Hot gas contemplated is superheated high pressure steam or recycled superheated converted crude gas.

6 Claims, 1 Drawing Sheet

(51) Int. Cl.
*C10J 3/54* (2006.01)
*C10J 3/56* (2006.01)
*C10J 3/46* (2006.01)
*C10K 1/00* (2006.01)
*C10K 1/10* (2006.01)
*C10K 3/04* (2006.01)
*C10K 3/06* (2006.01)
*C10G 2/00* (2006.01)

(56) References Cited

OTHER PUBLICATIONS

Carl J. et al: Noell-Konversionsverfahren zur Verwertung und Entsorgung von Abfällen, EF-Verlag für Energie- und Umwelttechnik GmbH, sections 2.2 and 2.3, 1994.

* cited by examiner

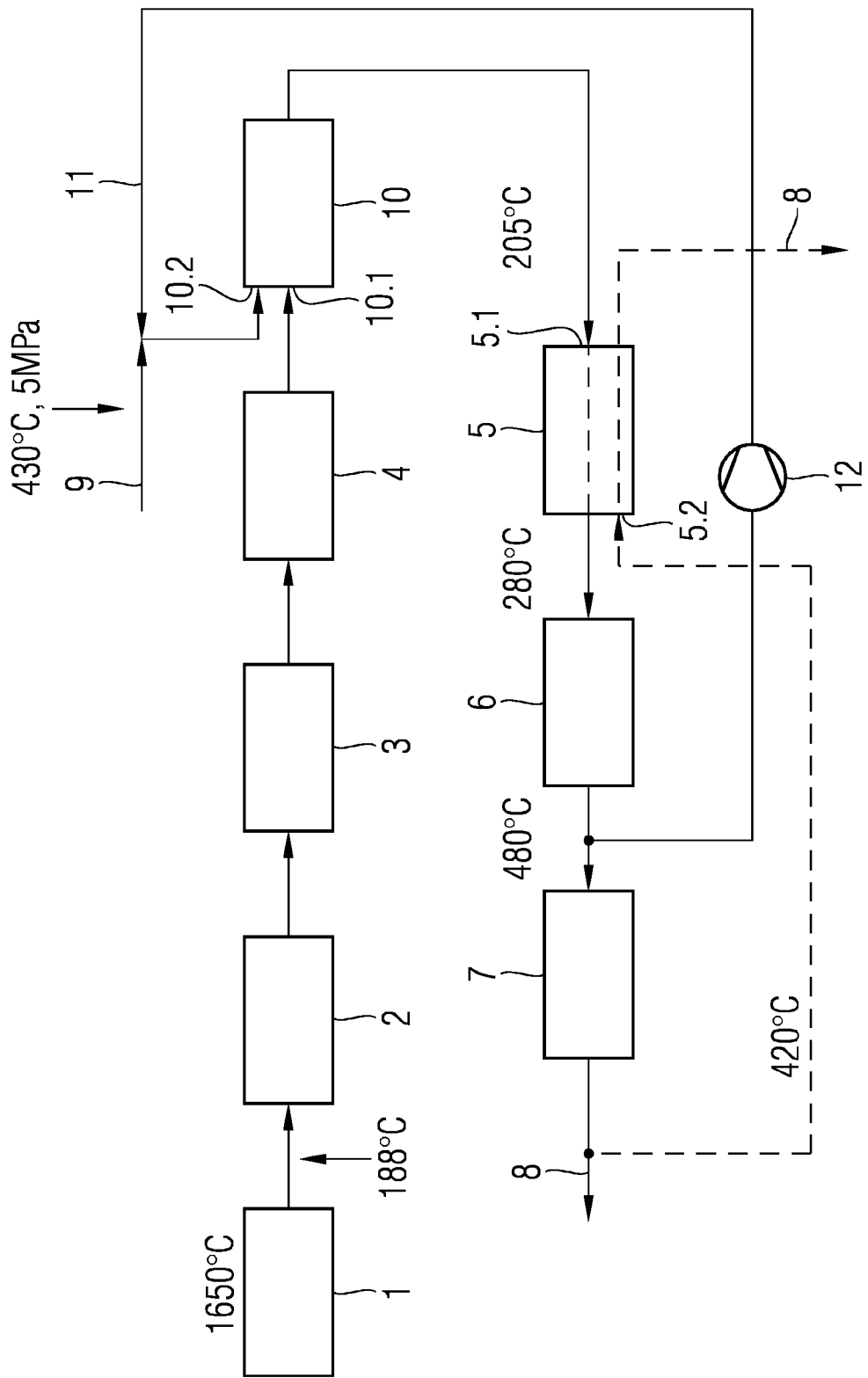

DEVICE FOR THE TREATMENT OF CRUDE SYNTHESIS GAS

CROSS REFERENCE TO RELATED APPLICATIONS

The present application claims priority of German Patent Application No. 102014203593.7, filed Feb. 27, 2014 and German Patent Application No. 102013215804.1, filed Aug. 9, 2013, the contents of which are incorporated by reference herein.

BACKGROUND OF THE INVENTION

1. Field of the Invention

The invention relates to a device for the processing of crude synthesis gas from a gasification facility, more particularly an entrained flow gasifier, which subjects fuels forming pulverized fuel to partial oxidation at temperatures of up to 1900° C. and under pressures of up to 10 MPa, for a crude gas converting operation.

2. Description of the Related Art

The invention is particularly suitable when the gasification proceeds as a partial oxidation of ashy liquid fuels or solid dusty fuels preferably under increased pressure of up to 10 MPa. Liquid fuels here may be ashy heavy oils from the refining of crude oil, or alternatively suspensions of pulverized fuels with water or with liquid hydrocarbons, referred to as slurries. Dusty fuels may be produced from coals in different degrees of coalification, from organic residues or biomasses, optionally after thermal pretreatment.

Reactors employed may be those having a refractory lining or having a cooled reaction chamber surround, as shown in patents DE 4446803 and EP 0677567. A description of the technology is found in J. Carl, P. Fritz "Noell-KONVERSIONSVERFAHREN" [Noell CONVERSION PROCESS], EF-Verlag 1994, sections 2.2 and 2.3, and also in "Die Veredlung and Umwandlung von Kohle" [Refining and Conversion of Coal] DGKM December 2008, M. Schingnitz, section on "GSP Processes". Undisrupted and continuous deposition of soot and of fine dust formed from slag is vital to reliable operation of catalytically operated processes for the processing of the crude gasification gas to form a synthesis gas that meets the requirements.

A description of the state of the art is given in DE 10 2005 041 930, for example.

Accordingly, the hot crude gas, carrying slag and dust, is transferred from the gasification chamber into a quenching chamber, and is cooled by injection of water to the pressure-dependent saturation temperature. This is about 190-220° C. in the case of an operating pressure of 4 MPa (40 bar), for example. From the quenching chamber, the steam-saturated crude gas and the granulated slag are taken off separately.

Located within the crude gas are particles of soot, of fine slag, of condensed salts introduced with the coal, and dusts in the particle size range of several hundred to <1 µm. They are removed by scrubbing processes to residual levels <1 mg/m³ (STP). This is done by subjecting the crude gas to intensive water scrubbing in different systems. Use is made, for example, of bubble, jet, and venturi scrubbers, more particularly in that order as well. To remove ultrafine salt mists, which likewise have disruptive consequences for downstream catalytic operations, high pressure water in ultrafine form is sprayed, or the crude gas is cooled slightly to produce a water mist—in both cases with large surface areas—in order to bind even ultrafine components. The crude gas thus cleaned can subsequently be heated further in heat exchangers and supplied, for example, to a catalytic crude gas converting operation for the establishment of the desired $H_2/CO$ ratio.

Experience shows that in spite of the arranging of a plurality of scrubbing stages operating on different principles, the deposition of ultrafine dust particles or ultrafine drops, in particular, from the spraying of scrubbing water is not achieved completely. Particularly affected is the availability of heat exchangers upstream of the crude gas converting operation, for preheating the crude gas in counter-current with hot converted gas from the scrubbing temperature, in the region of 190 to 220° C., to the converting temperature, of 270-300° C. As a result of the evaporation of the water on the hot heat exchanger tubes, the ash particles form solid crusts which hinder heat transfer and increase the pressure drops. It has further been found that calcium hydrogencarbonate dissolved in the water is converted into calcium carbonate, incorporates further fine particles, and causes the aforesaid crusting. The reaction equation responsible for this is as follows:

$$Ca(HCO_3)_2 \xrightarrow{heat} CaCO_3 + H_2O + CO_2$$

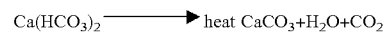

BRIEF SUMMARY OF THE INVENTION

Starting out from this prior art, it is an object of the invention to specify a device which allows sustained and undisrupted operation of a crude gas converting plant downstream of the crude gas scrubbing operation, without deposits and crusting hindering the operation of the upstream heat exchangers.

This object is achieved by means of a device.

In accordance with the invention, before entry of the steam-saturated crude gas, which carries with it water droplets and fine dust particles, into a heat exchanger of the crude gas converting plant, a device is provided which converts the crude gas from a saturated state into a superheated state by supplying hot gas or superheated steam, causing the entrained water droplets to evaporate. Surprisingly, it has been found that as a result of the conversion of bicarbonate into carbonate in the gas phase, the particulate solids lose their capacity to form solid crusts, pass through the heat exchanger together with the hot crude gas, and can be separated off in a mechanical deposition device before entry into the catalyst bed of the crude gas converting operation.

The invention is elucidated below, using two working examples, with reference to a FIGURE, to an extent as necessary for comprehension.

BRIEF DESCRIPTION OF THE DRAWING

The FIGURE shows the basic diagram of a device for the generation of synthesis gas or hydrogen by gasification of coal in an entrained flow.

DETAILED DESCRIPTION OF THE INVENTION

Two Examples are disclosed. The invention is not limited to specific embodiments disclosed in the Examples, but rather to the fullest scope of what the specific embodiments illustrate to one skilled in the art.

Example 1

In an entrained flow gasification plant with three gasification reactors, 240 t/h (tons per hour) of hard coal are gasified under a pressure of 4.1 MPa (41 bar) to generate 650 000 m³ (STP)/h of steam-saturated crude synthesis gas, which is cooled from 1650° C. to a saturation temperature of 188° C. by injection of water in a quenching chamber connected to the gasification reactor 1. Part of the injected quenching water is evaporated, and saturates the crude gas, while the excess quenching water is discharged from the quenching chamber together with granulated slag. The steam content of the crude gas is 36.9%. The crude gas likewise departing the quenching chamber carries with it a number of grams of dust per cubic meter, the particle size of said dust ranging from several mm down to fractions of a μm.

In order to ensure continuous operation of the synthesis gas production process, the dust should be removed as much as possible, ideally completely, ahead of the combination comprising heat exchanger 5 and crude gas converting operation 6. This is done by a series of scrubbing systems as per the prior art. First of all, in a preliminary scrubber 2, the coarse dust is removed, in order to prevent deposition and wear in downstream stages. Here it is possible to use cyclones, bubble scrubbers, or jet scrubbers. Subsequently, fixedly installed or regulatable venturi scrubbers 3 may be employed which remove dust particles down to a size of about 5 μm from the crude gas. For the further removal of fine dust and ultrafine dust, a fine-cleaning technology 4 is employed, which may be realized in the form of high-pressure condensate injection through nozzles or of partial condensation of the crude gas, with droplet removal in demisters. Also entrained are ultrafine water droplets containing dissolved calcium hydrogencarbonate. The total in this case is 5600 kg/h.

In order to evaporate the water droplets and thereby to superheat the crude gas by more than 5° C., the crude gas is supplied, ahead of the heat exchanger 5, with high pressure steam 9 in an amount of 37 000 kg/h at a temperature of 430° C. and at 5 MPa (50 bar), and this steam is mixed intensely with the crude gas using a static mixer 10, the crude gas, with a temperature of 205° C., being superheated by 17° C. In the heat exchanger 5, the crude gas is heated to the 280° C. entry temperature of the crude gas converting operation 6, in countercurrent with the converted crude gas which is at 420° C. The degree of conversion is guided by the desired $CO/H_2$ ratio in the subsequent pure gas. In the downstream acid gas scrubber 7, the crude gas is freed from $H_2S$, $CO_2$, and other harmful gases, and is available as pure synthesis gas 8 for syntheses of methanol, propellants, chemical intermediates, or else as hydrogen.

Example 2

Under the same conditions as in the example above, the superheating of the saturated crude gas is carried out with hot converted crude gas 11. In the converting plant, for the establishment of the desired $CO/H_2$ ratio, the crude gas is heated from the entrance temperature of 280° C., by means of the exothermic reaction, to an exit temperature of 480° C. Part of the converted crude gas is recycled via the hot gas circuit 11 and supplied to the crude gas via a static mixer 10 for the purpose of heating the crude gas, ahead of the heat exchanger 5, from 188° C. to 205° C. In order to overcome the pressure drop across the heat exchanger 5 and the catalyst bed of the crude gas converting operation 6, the hot gas blower 12 is used. For the heating of the crude gas to the stated 205° C. and the evaporation of the entrained 5600 kg of water, 69 200 m³ (STP)/h are recycled, corresponding to about 11% of the crude gas volume.

The invention also relates to a process for treating crude synthesis gas from a plant for the partial oxidation of fuels in an entrained flow gasifier, in which the steam-saturated crude gas, after a cascade of water scrubbers, is supplied to a crude gas converting operation, and the saturated crude gas, before entry into the crude gas converting operation, is heated in a heat exchanger to the entry temperature of the crude gas converting operation, against the hotter crude gas departing the crude gas converting operation, with the crude gas being converted from the steam-saturated into the superheated state before entry into the heat exchanger.

LIST OF REFERENCE NUMERALS 1 gasification with quenching
2 preliminary scrubber
3 venturi scrubber
4 fine cleaning
5 heat exchanger
5.1 first gas channel of heat exchanger 5
5.2 second gas channel of heat exchanger 5
6 crude gas converting operation
7 acid gas scrubber with cooling
8 pure synthesis gas
9 high pressure steam supply
10 static mixer
10.1 first entrance of mixer 10
10.2 second entrance of mixer 10
11 circuit for hot gas
12 hot gas blower

What is claimed is:

1. A device for treatment of crude synthesis gas from a facility for partial oxidation of fuels in an entrained flow gasifier, in which a path of the crude synthesis gas is in sequence of following stages, the device comprising:
    an entrained flow gasifier configured for supplying a steam-saturated crude synthesis gas,
    a cascade of water scrubbers receiving the steam-saturated crude synthesis gas and configured for cleaning the crude synthesis gas to remove dust particles therefrom,
    a mixer having a first entrance for receiving the cleaned crude synthesis gas from the water scrubbers, the mixer having a second entrance for receiving a supply of hot gas,
    the mixer having an exit for supplying superheated, unsaturated crude synthesis gas from the exit of the mixer;
    a heat exchanger having a first gas channel for receiving the crude synthesis gas from the exit of the mixer;
    a crude gas converting device receiving the crude synthesis gas from the heat exchanger, and
    an acid gas scrubber receiving the crude synthesis gas from the crude gas converting device,
    wherein
    the heat exchanger has a second gas channel for receiving the crude synthesis gas from the acid gas scrubber into the second gas channel of the heat exchanger,
    the second gas channel of the heat exchanger has an exit for the converted crude synthesis gas, and
    the mixer comprises a static mixer.

2. The device as claimed in claim 1, further comprising a heating device for heating the hot gas, the hot gas being comprised of superheated high pressure steam.

3. The device as claimed in claim 2, wherein the hot gas comprises a fraction of the superheated converted crude synthesis gas from the crude gas converting device.

4. The device as claimed in claim 3, further comprising a hot gas blower configured for supplying the fraction of the superheated converted crude synthesis gas from the crude gas converting device, the blower being in the second entrance of the mixer.

5. The device as claimed in claim 1, wherein the temperature of the superheated, unsaturated crude synthesis gas is 2 to 10° C. above the saturation temperature.

6. The device as claimed in claim 1, wherein a second of the cascade of water scrubbers removes dust particles from the crude synthesis gas which are finer than the dust particles removed from the crude synthesis gas by a first of the cascade of water scrubbers.

* * * * *